US005626570A

United States Patent [19]
Gallo

[11] Patent Number: 5,626,570
[45] Date of Patent: May 6, 1997

[54] OSTOMY APPLIANCE BELT

[76] Inventor: Kerry R. Gallo, 20733 Elberta Rd., Lynnwood, Wash. 98036

[21] Appl. No.: 661,626

[22] Filed: Jun. 11, 1996

[51] Int. Cl.$^6$ .................................................. A61F 5/44
[52] U.S. Cl. .............................................. 604/345; 2/49.2
[58] Field of Search ........................ 604/179, 332, 604/345; 2/49.2, 338, 920

[56] References Cited

U.S. PATENT DOCUMENTS

| | | |
|---|---|---|
| 1,857,179 | 5/1932 | Bowman . |
| 1,951,937 | 3/1934 | Judd . |
| 2,002,931 | 5/1935 | Bowman . |
| 2,476,513 | 7/1949 | Scott . |
| 2,583,721 | 1/1952 | Beede . |
| 2,688,327 | 9/1954 | Berg . |
| 2,778,362 | 1/1957 | Pollock et al. . |
| 2,788,785 | 4/1957 | Present . |
| 3,421,505 | 1/1969 | Freeman et al. . |
| 3,468,310 | 9/1969 | Kimball . |
| 4,533,355 | 8/1985 | Fair .................................. 604/345 |
| 4,738,661 | 4/1988 | Marut ............................... 604/179 |
| 4,888,006 | 12/1989 | Beaupied ......................... 604/345 |
| 5,026,362 | 6/1991 | Willett ............................. 604/345 |
| 5,135,520 | 8/1992 | Beaupied ......................... 604/345 |
| 5,142,702 | 9/1992 | Piloian ............................... 2/102 |
| 5,330,455 | 7/1994 | McKay ............................ 604/339 |

*Primary Examiner*—Robert A. Clarke
*Attorney, Agent, or Firm*—Dowrey & Associates

[57] ABSTRACT

An ostomy appliance belt for positively supporting and consealing an ostomy pouch as well as the stoma area of the user's abdomen. The belt is made from an elastic material and completely encircles the user's waist without interfering with the attachment of the ostomy appliance to the abdomen. The belt functions independently but cooperates with a self sealing ostomy appliance so as to permit removal and cleaning of the appliance without removal of the belt. A pocket forming elastic panel extends between the ends of the belt and covers the stoma area in the closed position. When the panel is opened, the ostomy pouch may be removed without removal of the belt.

10 Claims, 2 Drawing Sheets

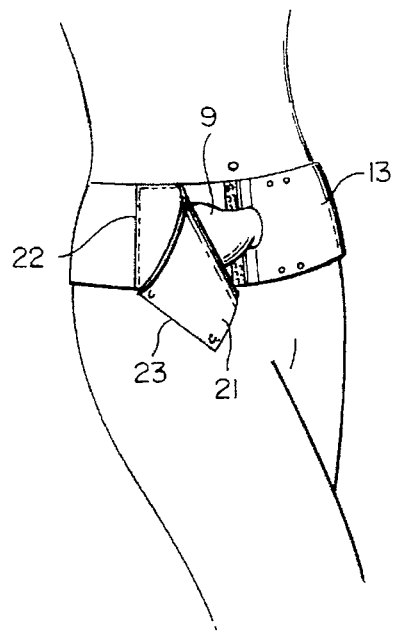
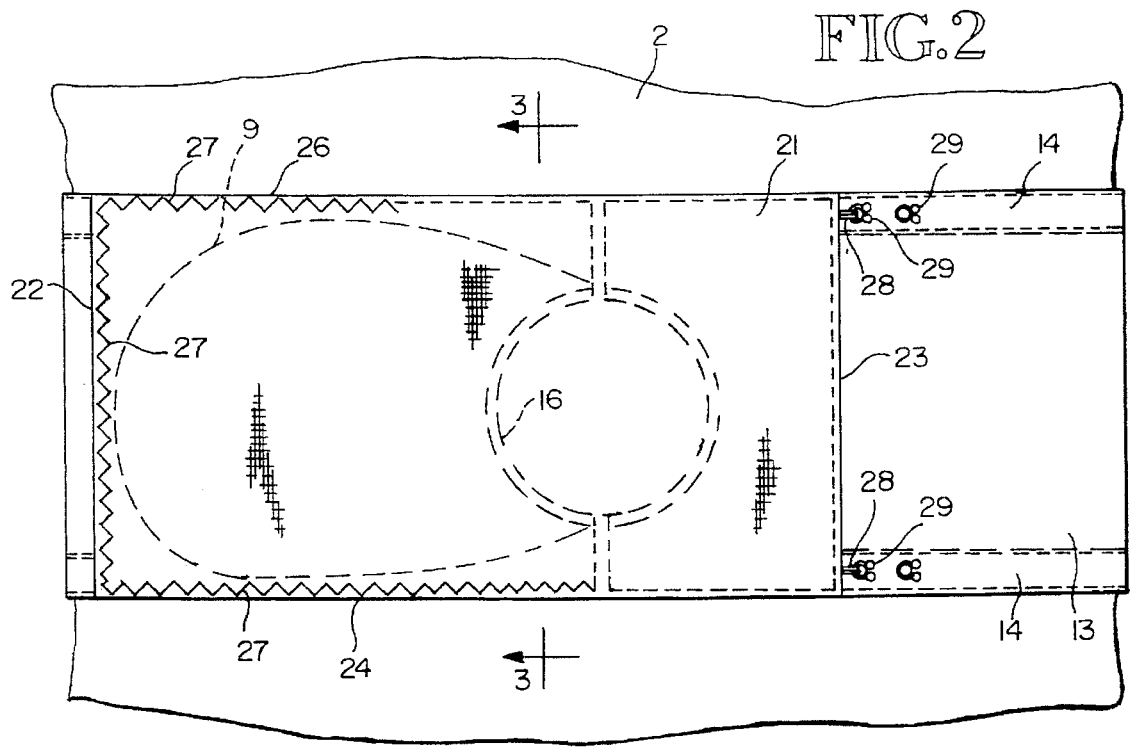

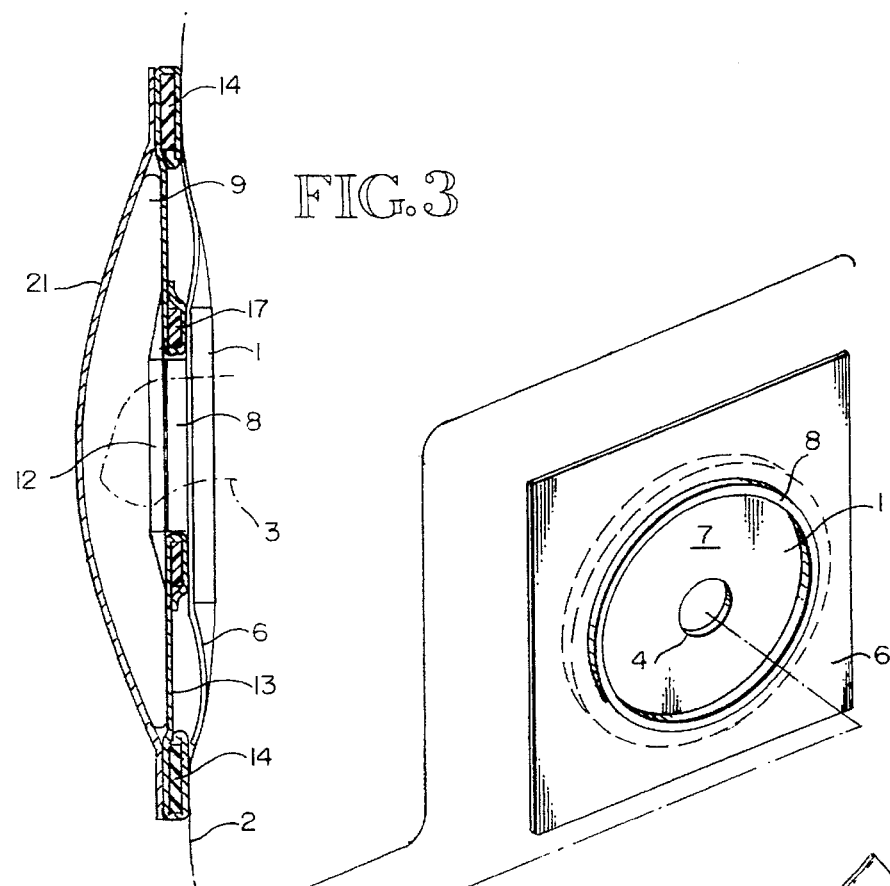
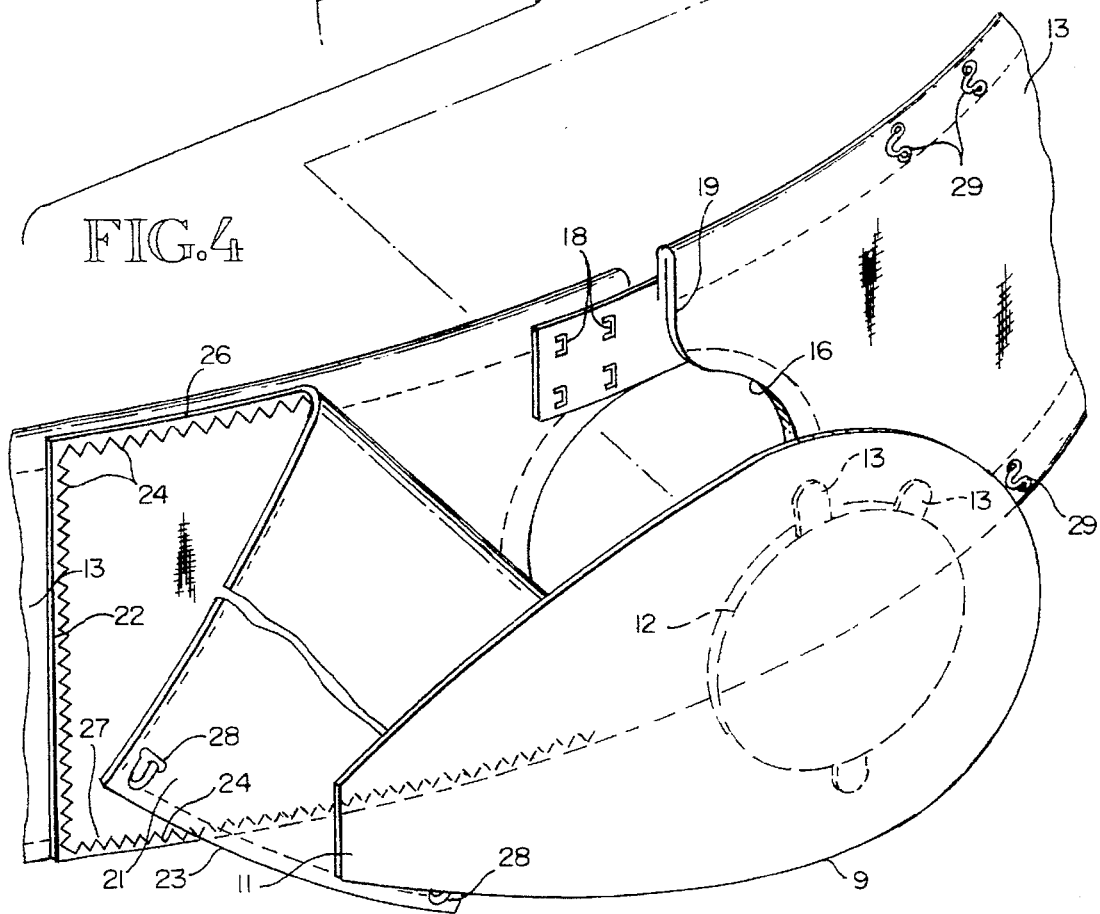

OSTOMY APPLIANCE BELT

BACKGROUND OF THE INVENTION

1. Field of the Invention

The present invention relates to a medical garment and more particularly to an improved support belt for securely supporting and covering an ostomy appliance. The belt is designed to support an ostomy collection bag or pouch in a secure position on the patient's abdomen without interfering with the functions of the ostomy appliance. The collection pouch is held completely covered and out of sight while allowing for expansion due to fecal discharge. The support provided permits the patient to engage in everyday activities including sports with complete confidence and comfort. The pouch remains readily accessible for removal and cleaning with minimum adjustment and without removal of the belt itself.

As used herein the term "ostomy" is intended to cover all types of procedures such as ileostomy and colostomy wherein a passageway is provided through the skin and a portion of the intestine or stoma is surgically connected thereto for discharge of fecal matter or for other purposes. In its broadest scope the invention relates to any surgical procedure requiring support of a bag, pouch or other container or apparatus for connection to a body entry device for receiving or discharging any substance.

2. Description of the Prior Art

Prior to the development of appliances for attachment to the exterior abdominal wall with sealed containers for collecting waste material draining from the patient's intestine, the common practice was to position a moisture proof, sometimes expandable, material against the abdominal wall to form a cavity between the abdominal wall and the material for collecting discharged waste matter. The following listed prior U.S. patents are examples of such devices:

| U.S. Pat. No. | Patentee |
| --- | --- |
| 1,857,179 | Bowman |
| 1,951,937 | Judd |
| 2,002,931 | Bowman |
| 2,688,327 | Berg |

As discussed in the Berg U.S. Pat. No. 2,688,327, it was also common practice to place an absorbent pad and/or deodorant substance in the collection cavity against the abdominal wall. Other substances such as tissues or the like were also used to collect and hold the waste material. The problems of personal hygiene, discomfort and activity limiting with the use of this type of device are readily apparent. The psychological effects on the patient were also severe.

With the advent of collection appliances which provide a separate pouch with an opening surrounding the stoma, various configurations of undergarments were devised for concealing and supporting the collection pouch. The following listed patents illustrate examples of this type of garment which also served to tightly hold the entry opening of the pouch against the wearer's abdomen, typically with elastic pressure as the only sealing means:

| U.S. Pat. No. | Patentee |
| --- | --- |
| 2,778,362 | Pollock et al |
| 3,421,505 | Freeman et al |
| 3,468,310 | Kimball |

Other devices of the same type utilized elastic belts which encircled the user's waist and applied pressure to hold the collection pouch opening against the abdomen wall surrounding the stoma. These devices in some instances also served to cover the collection pouch from view. The following U.S. patents illustrate such devices.

| U.S. Pat. No. | Patentee |
| --- | --- |
| 2,476,513 | Scott |
| 2,583,721 | Beede |
| 2,788,785 | Present |
| 5,330,455 | McKay |

With the advent of improved collection appliances having efficient sealing means for independently holding the collection pouch opening to the abdomen, about the stoma, the problem remains of comfort, support and concealment of the pouch. One common approach is to provide a supporting pocket built into a garment, usually a modified undergarment specially designed to conceal the pouch. the following U.S. patents illustrate examples of such garments.

| U.S. Pat. No. | Patentee |
| --- | --- |
| 4,533,355 | Fair |
| 4,888,006 | Beaupied |
| 5,135,520 | Beaupied |
| 5,142,702 | Piloian |

Problems with such garment type devices include uncomfortable placement of the pouch, inadequate support, bulkiness and the absence of any feeling of security against dislocation or exposure of the pouch.

In addition to the garment type support for separately sealed collection appliances, belt devices such as disclosed in the U.S. Pat. No. 5,026,362 to Willett have also been used. This type of support, however, provides no effective means for positively holding the collection pouch in a fixed position and provides little or no protection for the stoma area. Also of interest is U.S. Pat. No. 4,738,661 to Marut which, although not related to ostomy pouch holders, discloses a belt device with pocket means for holding an entrance tube connected to the wearer's stomach through a stoma. The pocket is designed to hold the outer distal end portion of the tube with absorbent material provided to absorb any excretions therefrom.

SUMMARY OF THE INVENTION

The ostomy appliance belt of the present invention provides an improved garment device for accomplishing positive support and concealment of an ostomy pouch which provides increased comfort and security to the wearer. The belt can be constructed from relatively inexpensive washable fabric material which is important for personal hygiene. The belt provides for easy access to the ostomy pouch and need not be removed during regular removal and cleaning of the pouch. The belt provides a fabric layer between the ostomy pouch and the wearer's skin for greater comfort and may be applied and removed completely independent of the ostomy appliance itself.

The features of concealment and security are extremely important to the recovering stoma patient following surgery. As will be appreciated by those who have experienced the surgery or who are knowledgeable about patient recovery, restoration of self image and a more positive body image is extremely important and is an essential part of recovery from this particular surgery. The use of the ostomy belt of the present invention aids the patient in avoiding the extreme depression experienced following surgery and in building sufficient confidence to again enter into normal everyday pursuits such as sports, dancing, walking, swimming and intimate relationships with other persons.

BRIEF DESCRIPTION OF THE DRAWINGS

FIG. 1 illustrates the positioning of the ostomy belt on the body of an ileostomy patient;

FIG. 2 is a frontal elevational view of the ostomy belt with the ostomy pouch and pocket in the closed position;

FIG. 3 is a cross sectional view taken along lines 3—3 of FIG. 2; and

FIG. 4 is an exploded view showing the relationship between the ostomy appliance and the assembled ostomy belt of the present invention.

DESCRIPTION OF THE PREFERRED EMBODIMENT

The ostomy belt according to the present invention will be illustrated and described as it is utilized with an ileostomy appliance. It will be understood, however, that the belt may be used in connection with any surgical procedure which provides a stoma in the abdominal wall for discharging or receiving any substance. Although the details of the ostomy appliance may vary depending upon the supplier, the ostomy appliance utilized in connection with the present invention and illustrated in the drawings is commercially available and sold under the trademark SUR-FIT Flexible® distributed by ConvaTec, a Bristol-Myers Squibb Company. This appliance includes a central disc approximately 2½ inches in diameter for direct application to the patient's skin with a central opening for accommodating the stoma and with means being provided to seal the disc to the patient's skin. The disc is also held to the patient's skin by means of surgical adhesive tape attached to and surrounding the disc. The disc is provided with a receptor ring for sealing engagement with a mating plastic fitting connected to the stoma pouch. This interconnection allows the disc to be adhesively fixed on the patient's skin and for the stoma pouch to be removed, replaced or cleaned and refitted on the disc without removal of the disc.

FIGS. 3 and 4 illustrate the details of the ostomy appliance. In FIG. 3 the ostomy appliance, including the central disc and the collection pouch, is shown in elevation while the support belt of the present invention has been cross-sectioned for clarity. As shown in FIG. 3, the central disc 1 is applied directly to the patient's skin surface on the abdominal wall 2 and surrounds the stoma 3 in a well known manner. The central disc 1 may be made of various substances but will usually consist of a wax-like deformable material which may be pressed against and conformed to the patient's skin surface. In some instances, a sealing compound may be utilized between the back surface of the disc 1 and the skin surface area to enhance the adherence of the disc to the stomach wall and to positively seal against any escape of moisture. The disc 1 is provided with a central opening 4 which may be enlarged if necessary to accommodate the stoma of the individual patient. This is usually done by the user at the time of application.

The disc 1 is fitted with an enlarged area adhesive tape patch 6 around its outside peripheral edge area for further securing the disc to the skin area around the stoma. The adhesive tape patch 6 is strongly adhered to or incorporated in the material of the disc 1 at the time of manufacture by known means and serves to further hold the central disc in fixed position and to seal against any escape of moisture. The outside surface 7 of the disc 1 is provided with a continuous annular plastic sealing ring 8 attached to and imbedded in the material of the disc at time of manufacture. The bond between the ring 8 and the outside surface 7 of the disc is moistureproof and extremely strong so as to ensure against any possibility of separation during use of the appliance.

The collection pouch 9 is usually constructed form light weight plastic film which is moisture impervious and includes an open end 11 which is used for emptying the pouch and which is normally closed by means of a tie string or the like, not shown. The pouch 9 has an opening in one wall to which is attached a plastic receptor ring 12. The ring 12 may be attached to the wall of the plastic pouch by any known means such as adhesive or heat sealing so as to be watertight. The receptor ring 12 includes an annular continuous channel which is sized so as to sealingly receive the male sealing ring 8 on the surface of the disc 1. This mating engagement is not shown in detail since it is a well known sealing expedient commonly used in plastic container lids and the like. The collector pouch is mounted on the central disc 1 simply by snapping the receptor ring onto the male sealing ring 8. The rim of the ring 12 may include one or more pull tabs 13 for facilitating the removal of the pouch for cleaning or replacement.

It will be understood that the foregoing described ostomy appliance structure is a commercially available appliance, the details of which form no part of the present invention. The requirement for use in combination with the present support belt is that the ostomy appliance be independently mountable and sealed to the user's abdominal wall independent from the application of the support belt presently to be described.

The support belt of the present invention comprises a single length, relatively wide band of elastic belt material 13 for extending completely around the user's waist as shown in FIG. 1. The belt may be constructed of any elastic fabric such as commercially available cotton lycra or equivalent material. The elastic material of the belt should be chosen so as to be washable for reasons of personal hygiene. Although the width dimensions of the belt may be varied, it has been found that a band of cotton lycra approximately 7 inches wide provides excellent belting material for use in combination with the particular ostomy appliance described. In addition to the elasticity of the belting material 13 it may also be desirable to incorporate elastic bands 14 in the upper and lower edges of the belt fabric 13 as illustrated. Elasticity may also be provided in the connector means between the opposite ends of the belt and, in some instances, a flexible fabric alone may suffice so long as a snug fit and the required support are provided. The belt may be hemmed and stitched in any well known manner.

Each end of the belt 13 is provided with a substantially semi-circular cut-out portion 16 to allow the ends of the belt to be attached about the waist while accommodating the circular attaching and sealing engagement between the collection pouch 9 and the disc 1 without interference. If desired, the contour of the cut-out portion 16 may be slightly stiffened by means of some form of rigid plastic or other material 17 sewn or otherwise attached into the hem of the cut-out portion 16. This arrangement is shown most clearly in FIG. 3. The stiffener material 17 will serve to prevent interference between the ends of the belt material and the seal between the collection pouch and the disc 1. The ends of the elastic belt 13 are connected by means of hook and eye fasteners 18 sewn onto suitable tabs on the opposite ends of the belt 13. As shown in FIG. 4, the eyes 18 are designed to be connected to suitable hooks, not shown, on the backside of the end 19 of the upper edge of the belt 13. The hooks may be mounted on special tabs or sewn to the back surface of the end of the belt 13 as desired. It will be understood that the mating surfaces of the bottom edges of each end of the belt will also be provided with hook and eye connectors in the manner described. In order to provide a degree of adjustment, several spaced rows of hooks such as hooks 18 may be used and any number of rows of these hooks and eyes may be adapted for any particular use. Other forms of well known connectors or connecting means may be used so long as a positive and reliable connection is provided, preferably with some feature of adjustment as described for the user's comfort.

A pocket forming fabric panel 21 is sewn or otherwise attached to the outside face of one end of the fabric belt 13 as illustrated most clearly in FIG. 4. The fabric of the panel 21 may be identical to the elastic material of the belt 13 and in any case the panel 21 will be flexible and elastic to accommodate filling of the pouch. If a non-elastic material is used, some means of expansion of the pouch pocket should be provided. As seen in FIG. 4, the left edge 22 is attached along its entire length to the front face of the fabric belt 13 and the opposite or right hand edge 23 is left unattached. As seen most clearly in FIGS. 1 and 2, the pocket panel 21 extends over a portion of one end of the belt 13 substantially the length of the collection pouch 9 and beyond the associated end 16 so as to overlap the opposite end of the belt to an extent at least sufficient to cover the ostomy appliance. The bottom edge 24 of the panel is stitched or otherwise attached to the remaining extent of the bottom edge of the associated belt end. The top edge 26 of the panel is stitched or otherwise attached to the upper edge of the associated end of the belt only approximately ½ the distance between the left end 22 of the panel and the end of the belt. This arrangement is illustrated by the stitching lines 27 in FIGS. 2 and 4. In this manner, the panel 21 in the embodiment illustrated forms a pocket for reception of substantially the entire length of the collection pouch 9. The stitching 27 on the bottom, one end and on the partial upper edge of the panel 21 define this pocket.

The right end of the panel 21, as shown in FIG. 2, extends across the opposite end of the belt and is attached to the belt 13 by means of the hooks 28 and eyelets 29 or any other suitable connector means, in a well known manner. As illustrated, both the top and bottom edges of the panel 21 and the belt 13 may be provided with hook and eye attachments. In this manner, the collection pouch 9, as well as the connection of the pouch to the abdominal wall, are completely covered and concealed. The collection pouch is securely contained in the elastic pocket formed by the panel 21 and the fabric of the end of the belt 13 as shown in FIG. 2. This arrangement is enhanced by the fact that the pouch 9, although generally oblong in shape, may be attached in any position of rotation because of the detachable sealing ring arrangement. The pouch is thus directed laterally into the pocket formed by the panel 21. It will be obvious that the mounting of the panel and forming of the pocket on the front face of the belt may be reversed from the left hand arrangement shown in the present drawings to the opposite side or right side mounted position so as to accommodate either right hand or left hand directed pouches. With this arrangement, the fabric of the belt 13 also provides a barrier between the user's skin surface and the pouch for reasons of comfort.

Although a preferred embodiment of the invention has been shown and described herein with certain specific modifications, it is understood that the present disclosure is made by way of example and that various other embodiments and modifications are possible without departing from the inventive concept and are included within the scope of the following claims, which claimed subject matter is regarded as the invention. The aim of the appended claims therefor is to cover all such changes and modifications as fall within the true spirit and scope of the invention.

What is claimed is:

1. An ostomy belt for supporting an ostomy apparatus connected to an ostomy appliance comprising, in combination;

an elongated waist-encircling band of elastic material having a front surface with end connectors and cut-out areas in the terminal ends for accommodating an ostomy appliance, a pocket forming elastic fabric panel connected to said front surface on one terminal end area of said band to form an ostomy apparatus support pocket, and a flap on said panel having a free end sized to extend across said terminal ends and being connectable to the other end of the band when the band is secured about the wearer's waist, whereby said flap may be connected to said other end of the band to close said pocket and conceal said ostomy appliance.

2. An ostomy belt for covering an ostomy appliance and supporting an ostomy apparatus connected thereto comprising in combination;

an elongated waist-encircling band of flexible material, said band including band connectors on the terminal ends thereof and cut-out areas to accommodate an ostomy appliance on the wearer's abdomen, a pocket forming panel attached to the end area of one terminal end of the band for supporting an ostomy apparatus carried by said appliance with a flap member having a free end sized for overlying the terminal ends of the band and said ostomy appliance, and flap connectors on the free end of said flap and said band for securing the flap to the band when the band is secured about the wearer's waist to thereby close said pocket to support said ostomy apparatus and conceal said ostomy appliance.

3. The ostomy belt of claim 2 wherein;

said band comprises an elastic fabric, said band connectors being adjustable to vary the effective length of said band, said panel comprises an elastic fabric, and said flap connectors being adjustable to vary the capacity of said pocket.

4. The ostomy belt of claim 3 wherein said cut-out areas are located in the end edge of each terminal end of the band and are semi-circular in shape to accommodate the connection between the appliance and the ostomy apparatus.

5. The ostomy belt of claim 4 wherein said ostomy apparatus comprises an ostomy collection pouch, said panel being sized to accommodate said pouch and to expand with filling of the collection pouch.

6. The ostomy belt of claim 5 wherein said band includes an inside surface for contacting the skin of the user and an outside surface for mounting said panel, said panel comprising an elongated body connected to the front surface of the band about a sufficient extent of its peripheral edges to form a pocket with said front surface for receiving and supporting said ostomy apparatus.

7. An ostomy belt for a stoma patient fitted with an ostomy appliance, said appliance having a base member located on the abdominal surface area and independently sealed thereto about the stoma, said appliance including a removable ostomy apparatus having a moisture sealed connection to the base member and being in communication with the stoma, said appliance belt supporting and concealing the ostomy apparatus and stoma area without attachment thereto, comprising;

a relatively wide elongated band of flexible material having a front surface and a back surface for contacting the patient's skin with connectors on the terminal ends thereof for forming a waist-encircling belt in the area of the stoma, said band being constructed of sufficient width to cover the area of the ostomy appliance and including first and second abutting terminal ends with end edges having opposing cut-out areas to allow for positioning and exposure of the sealing connection between the appliance base and the removable ostomy apparatus without interference therewith, connector members associated with the terminal ends of the band for securing the band about the patient's waist, whereby said ostomy apparatus may be removed without removal of the band, a pocket forming panel connected to one terminal end area of said band and including a free end flap sized to overlap the abutting ends of said band when the band is secured about the patient's waist, said panel being connected to the front surface of the band about a sufficient extent of its peripheral edges to form a pocket with said front surface for receiving and supporting said ostomy apparatus, and connector means mounted on said flap and the front surface of the other end of said band adjacent said abutting edges for securing the flap to the band to thereby close said pocket and completely conceal said ostomy appliance.

8. The ostomy belt of claim 7 wherein;

said band comprises an elastic fabric, said band connectors being adjustable to vary the effective length of said band, said panel comprises an elastic fabric, and said flap connectors being adjustable to vary the capacity of said pocket.

9. The ostomy belt of claim 8 wherein said cut-out areas are substantially semi-circular in shape to accommodate said sealing connection.

10. The ostomy belt of claim 9 wherein said ostomy apparatus comprises an ostomy collection pouch, said panel being sized to accommodate said pouch and to expand with filling of the collection pouch.

* * * * *